US010265479B2

(12) United States Patent
Plumptre et al.

(10) Patent No.: US 10,265,479 B2
(45) Date of Patent: Apr. 23, 2019

(54) DRUG DELIVERY DEVICE

(71) Applicant: SANOFI-AVENTIS DEUTSCHLAND GMBH, Frankfurt am Main (DE)

(72) Inventors: David Aubrey Plumptre, Worcestershire (GB); Thomas Frederick Osman, Long Itchington (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 239 days.

(21) Appl. No.: 15/138,533

(22) Filed: Apr. 26, 2016

(65) Prior Publication Data
US 2016/0235923 A1 Aug. 18, 2016

Related U.S. Application Data

(63) Continuation of application No. 14/423,732, filed as application No. PCT/EP2013/067860 on Aug. 29, 2013, now Pat. No. 9,345,841.
(Continued)

(30) Foreign Application Priority Data

Aug. 31, 2012 (EP) ..................................... 12182564

(51) Int. Cl.
*A61M 5/24* (2006.01)
*A61M 5/315* (2006.01)
*A61M 5/31* (2006.01)

(52) U.S. Cl.
CPC .......... *A61M 5/31543* (2013.01); *A61M 5/24* (2013.01); *A61M 5/3157* (2013.01);
(Continued)

(58) Field of Classification Search
CPC ................ A61M 5/24; A61M 5/31551; A61M 5/31541; A61M 5/31585;
(Continued)

(56) References Cited

U.S. PATENT DOCUMENTS 533,575 A 2/1895 Wilkens
4,865,591 A 9/1989 Sams
(Continued)

FOREIGN PATENT DOCUMENTS

CA 2138528 C 12/1998
CA 2359375 A1 7/2000
(Continued)

OTHER PUBLICATIONS

Russian Office Action for RU App. No. 2015111241, dated Aug. 31, 2017.
(Continued)

*Primary Examiner* — Imani N Hayman
*Assistant Examiner* — Tiffany Legette
(74) *Attorney, Agent, or Firm* — Fish & Richardson P.C.

(57) ABSTRACT

The invention relates to a reusable drug delivery device for selecting and dispensing a number of user variable doses of a medicament. The device comprises a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver.

13 Claims, 6 Drawing Sheets

Related U.S. Application Data

(60) Provisional application No. 61/696,496, filed on Sep. 4, 2012.

(52) U.S. Cl.
CPC .... *A61M 5/31511* (2013.01); *A61M 5/31515* (2013.01); *A61M 5/31528* (2013.01); *A61M 5/31541* (2013.01); *A61M 5/31548* (2013.01); *A61M 5/31551* (2013.01); *A61M 5/31568* (2013.01); *A61M 5/31585* (2013.01); *A61M 5/31593* (2013.01); *A61M 2005/2488* (2013.01); *A61M 2005/3125* (2013.01); *A61M 2005/3126* (2013.01); *A61M 2205/581* (2013.01); *A61M 2205/585* (2013.01)

(58) Field of Classification Search
CPC ........ A61M 2205/581; A61M 5/31543; A61M 5/3158; A61M 2005/2488; A61M 5/3155; A61M 5/31525; A61M 5/31568; A61M 2005/3126; A61M 5/31586
See application file for complete search history.

(56) References Cited

U.S. PATENT DOCUMENTS

| | | | |
|---|---|---|---|
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 7,955,303 B2 | 6/2011 | Burren et al. | |
| 8,187,233 B2 | 5/2012 | Harms et al. | |
| 8,317,757 B2 | 11/2012 | Plumptre | |
| 9,005,171 B2 | 4/2015 | Jones | |
| 9,089,651 B2 | 7/2015 | Butler et al. | |
| 9,345,841 B2 * | 5/2016 | Plumptre | A61M 5/24 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0016143 A1 | 1/2007 | Miller et al. | |
| 2007/0123829 A1 | 5/2007 | Atterbury et al. | |
| 2008/0306445 A1 | 12/2008 | Burren et al. | |
| 2009/0275916 A1 | 11/2009 | Harms et al. | |
| 2010/0324495 A1 | 12/2010 | Jones | |
| 2011/0092905 A1 | 4/2011 | Cowe | |
| 2012/0143146 A1 | 6/2012 | Strehl et al. | |
| 2012/0165744 A1 | 6/2012 | Jones | |
| 2012/0165750 A1 | 6/2012 | Plumptre | |
| 2012/0172809 A1 | 7/2012 | Plumptre | |
| 2012/0289908 A1 | 11/2012 | Kouyoumjian et al. | |
| 2013/0197448 A1 | 8/2013 | Butler et al. | |
| 2013/0211327 A1 | 8/2013 | Osman et al. | |
| 2013/0267905 A1 | 10/2013 | Teucher et al. | |
| 2015/0057619 A1 | 2/2015 | Osman et al. | |
| 2015/0065960 A1 | 3/2015 | Osman | |
| 2017/0043098 A1 | 2/2017 | Kohlbrenner et al. | |

FOREIGN PATENT DOCUMENTS

| | | | |
|---|---|---|---|
| EP | 0496141 A1 | 7/1992 | |
| EP | 0897729 A2 | 2/1999 | |
| EP | 0937471 | 8/1999 | |
| EP | 0937476 | 8/1999 | |
| EP | 1776975 A2 | 4/2007 | |
| JP | 2010-503433 A | 2/2010 | |
| JP | 2011-519600 A | 7/2011 | |
| RU | 2214286 C2 | 10/2003 | |
| WO | 93/07922 A1 | 4/1993 | |
| WO | 93/24160 A1 | 12/1993 | |
| WO | 99/38554 | 8/1999 | |
| WO | 01/10484 | 2/2001 | |
| WO | 02/30495 A2 | 4/2002 | |
| WO | 02/092153 A2 | 11/2002 | |
| WO | 03/080160 A1 | 10/2003 | |
| WO | 2006/084876 A1 | 8/2006 | |
| WO | 2009/132778 A1 | 11/2009 | |
| WO | 2010/139691 | 12/2010 | |
| WO | 2011/039236 | 4/2011 | |
| WO | WO 2011039236 A1 * | 4/2011 | ........ A61M 5/31543 |
| WO | WO 2011039203 A3 * | 6/2011 | ........ A61M 5/31543 |
| WO | 2011/154489 A1 | 12/2011 | |

OTHER PUBLICATIONS

International Search Report for Int. App. No. PCT/EP2013/067860, completed Dec. 17, 2013.
Japanese Office Action for JP Application No. 2015-529016, dated Jul. 4, 2017.
"Pen-injectors for medical use—Part 1: Pen-injectors—Requirements and test methods," International Standard, reference No. ISO 11608-1:2000(E), first edition Dec. 15, 2000, 32 pages.

* cited by examiner

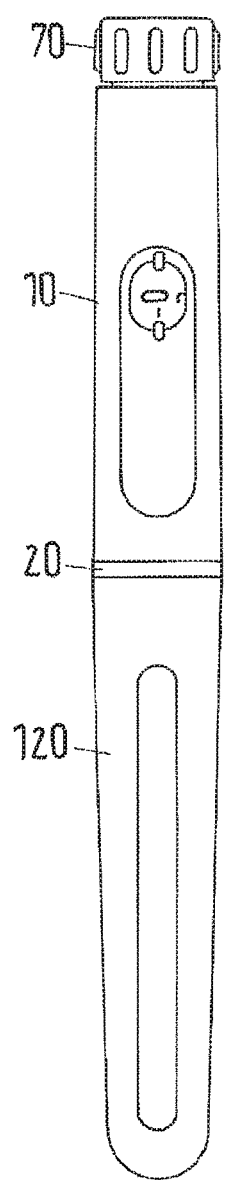
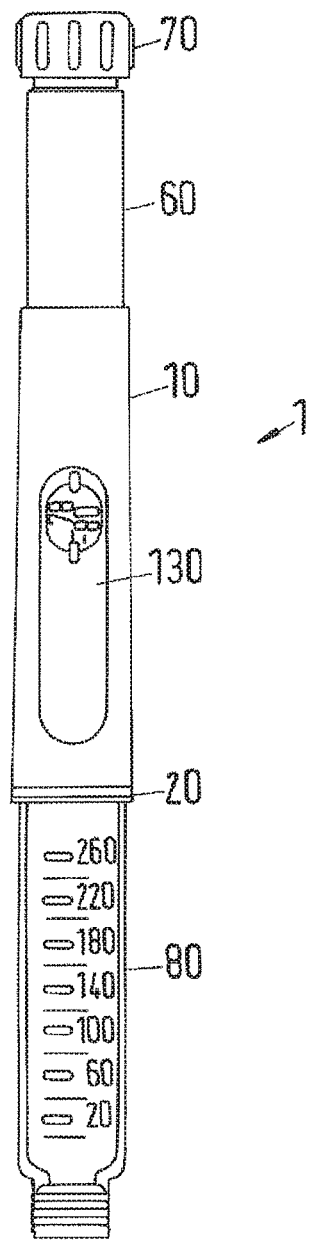

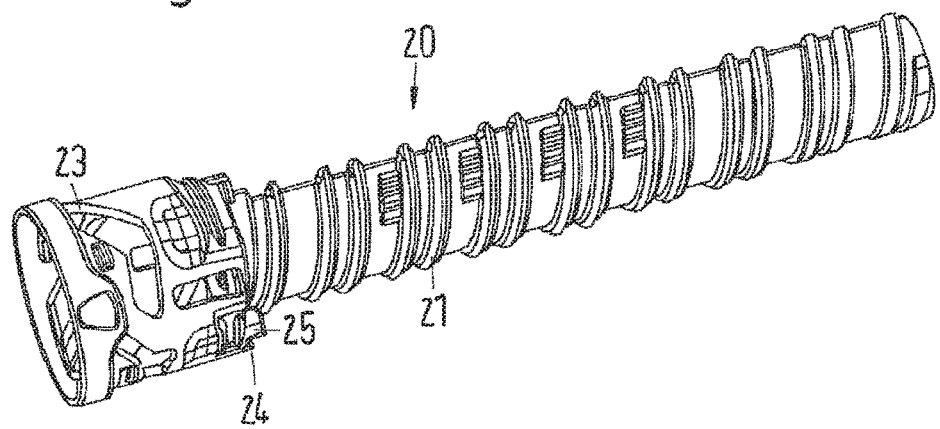
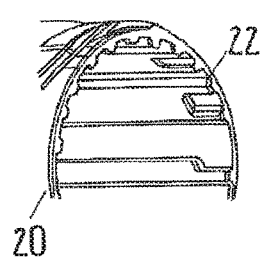
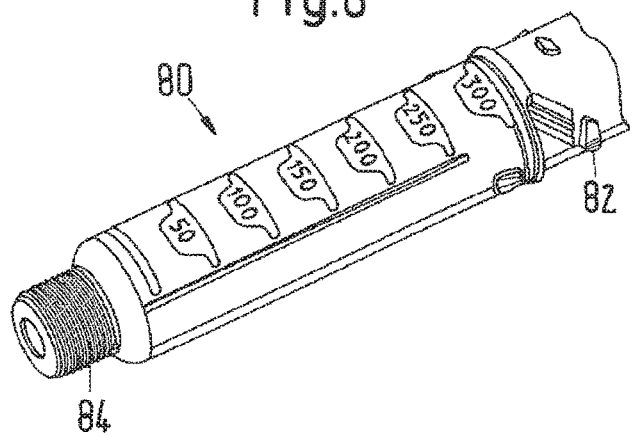
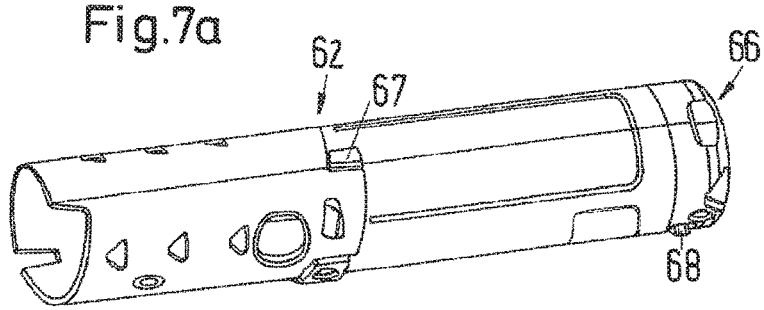
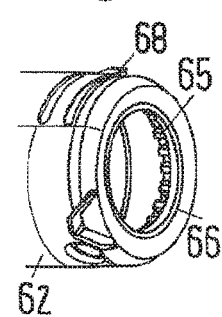

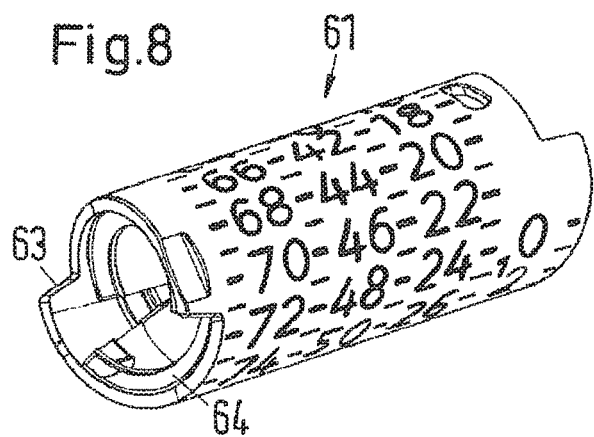
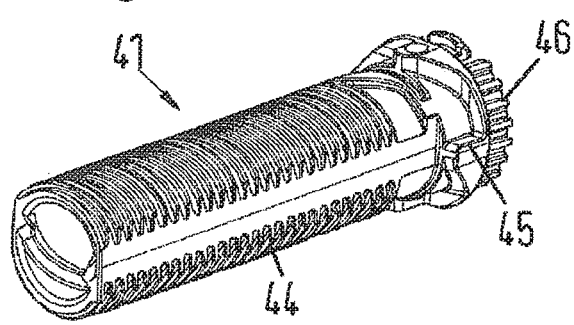
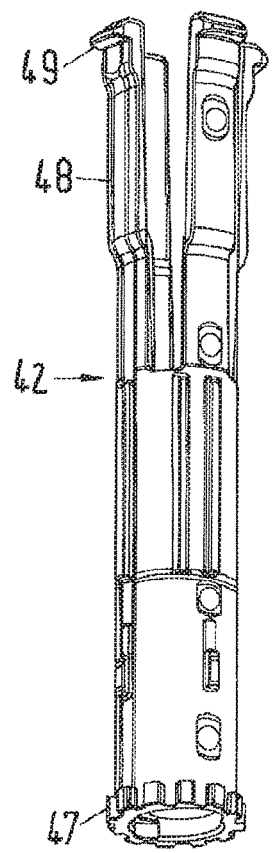
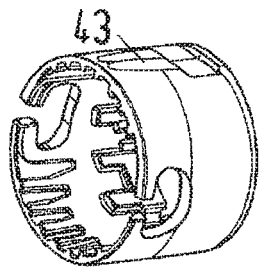
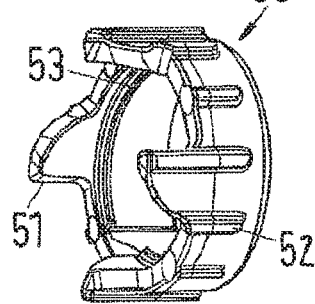

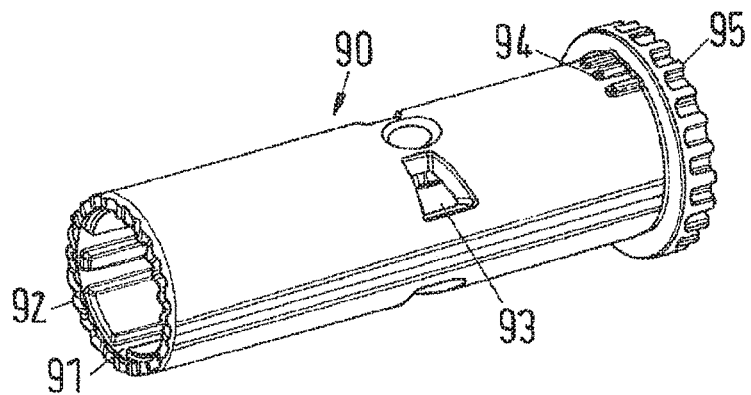
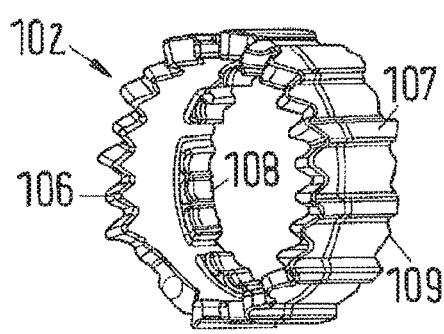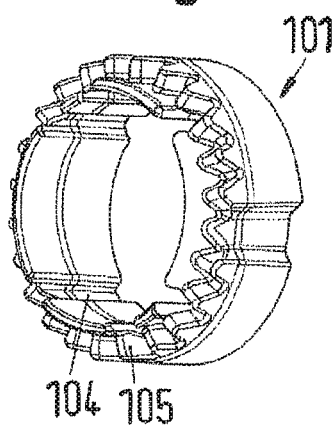
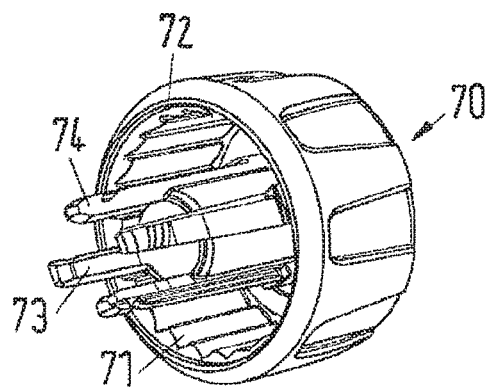

DRUG DELIVERY DEVICE

CROSS REFERENCE TO RELATED APPLICATIONS

The present application is a continuation of U.S. patent application Ser. No. 14/423,732, filed Feb. 25, 2015 which is a U.S. National Phase Application pursuant to 35 U.S.C. § 371 of International Application No. PCT/EP2013/067860 filed Aug. 29, 2013, which claims priority to European Patent Application No. 12182564.0 filed Aug. 31, 2012, and U.S. Provisional Patent Application No. 61/696,496, filed Sep. 4, 2012. The entire disclosure contents of these applications are herewith incorporated by reference into the present application.

TECHNICAL FIELD

The present invention is generally directed to drug delivery devices. More particularly, the present invention is directed to reusable drug delivery devices.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

For reusable drug delivery devices it is necessary to allow the piston rod or lead screw to be reset, i.e. pushed and/or wound back into the device, during the step of replacing an empty cartridge by a new (full) cartridge. In addition, many drug delivery devices comprise a dose limiter for preventing the setting of a dose, which exceeds the amount of liquid left in a cartridge of the drug delivery device. If such a dose limiter is provided, this dose limiter mechanism has to be reset, too.

In the following resetting of the device is to be understood the act of replacing or exchanging a cartridge involves a retraction of the piston rod or lead screw and, if present, bringing the dose limiter (last dose protection mechanism) back into an initial configuration allowing dose setting.

It is an object of the present invention to provide an improved reusable drug delivery device.

SUMMARY

According to a first embodiment of the present invention, this object is solved by a drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, a clutch for rotationally coupling the driver to the housing or the display member and a button rotationally coupled to the display member and to the driver, wherein the driver is in threaded engagement with the piston rod, permanently rotationally locked to the button, axially displaceable relative to the button and comprises at least two separate components which are rotationally coupled during dose setting and during dose dispensing and which are rotationally decoupled during resetting of the device. Decoupling of the two driver components during resetting has the benefit that both, the piston rod, which is in threaded engagement with the driver, and a dose limiter mechanism, which usually acts on the driver, can be reset together by spinning one of the driver components whereas the other remains stationary in the device. The driver may comprise a third component for coupling the first and second components during dose setting and dose dispensing.

According to a second embodiment of the present invention, this object is solved by a drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, a clutch for rotationally coupling the driver to the housing or the display member and a button rotationally coupled to the display member and to the driver, wherein the display member has a distal end provided with an inwardly protruding thread and a proximal end provided with an inwardly protruding flange, wherein the display member comprises two separate components with a first component comprising the thread and the other component comprising the flange. The display member has to be coupled to the housing and to the driver. The construction of the display member with two inwardly directed engaging features avoids a bulky design of the device which would be the result if one engagement feature would be on the outside and the other would be on the inside of the display member. In addition, the inwardly directed engagement features make it possible to provide further functions on the outer surface of the display member, e.g. limiting stop elements. Providing two separate components, which are preferably axially and rotationally constrained, makes production of the display member more efficient and easier. Preferably, the display member has a series of numbers or the like symbols arranged on its outer surface for indicating a set dose. If the display member is in threaded engagement with the housing, the numbers or the like may be arranged on a helical path.

According to a third embodiment of the present invention, this object is solved by a drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, a clutch for rotationally coupling the driver to the housing or the display member and a button rotationally coupled to the display member and to the driver, wherein the button comprises fingers which engage corresponding slots of the driver for rotationally coupling the button to the driver and which comprise snap features engaging corresponding snap features of the clutch for axially coupling the button to the clutch. In other words, the driver and the button are rotationally coupled by a dog clutch or claw coupling with the fingers of the button having the additional function of axially constraining the button to the clutch member. This additional function in one component reduces the number of component parts of the device and assembling complexity.

According to a fourth embodiment of the present invention, this object is solved by a drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, a clutch for rotationally coupling the driver to the housing or the display member and a button rotationally coupled to the display member and to the driver, wherein the driver comprises fingers which engage corresponding slots of the button for rotationally coupling the button to the driver and which comprise hook features engaging corresponding contact features of the display member for axially coupling the driver to the display member. In other words, the driver and the button are rotationally coupled by a dog clutch or claw coupling with the fingers of the driver having the additional function of axially engaging the display member, e.g. for entraining the display member during dose dispensing. This additional function in one component reduces the number of component parts of the device and assembling complexity.

According to a fifth embodiment of the present invention, this object is solved by a drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, a clutch for rotationally coupling the driver to the housing or the display member and a button rotationally coupled to the display member and to the driver, wherein the button comprises a ring of clicker teeth engaging a corresponding clicker feature of the display member at least during dose dispensing. The clicker produces a tactile and/or audible feedback during use of the device and is usually provided with at least one separate component. In the present embodiment of the invention, these functions of the device are realized without adding component parts. Preferably, the display member comprises an elastically deformable finger having a protrusion for engaging the clicker teeth. An additional clicker may be provided, which is active during dose setting.

Preferably, the piston rod is a double threaded piston rod having a first outer thread engaging an internal thread of the housing and a second outer thread engaging an internal thread of the driver, wherein the first and second outer threads may overlap each other at least partially. This allows providing a mechanical advantage, i.e. a transmission (gear) ratio, in the device. Typically, the dial extension of the button, i.e. the distance the button winds out of the housing during dose setting, will be larger than the distance the piston rod is displaced relative to the cartridge holder and thus the cartridge. This allows dispensing even small amounts of a medicament with a maximum of dispensing control by the user. The first and second outer threads may have a different pitch. However, it is preferred if the first and second outer threads have the same pitch but are oppositely directed.

One of the outer threads of the piston rod may be in engagement with a corresponding inner thread of the housing, preferably an inner housing body. Thus, the piston rod rotates both, during dose dispensing and during resetting of the device, i.e. when the piston rod is pushed (wound) back.

A further reduction of the number of component parts may be achieved if the piston rod comprises a bearing attached to the piston rod by at least one predefined breakage point. The bearing is axially constrained but rotatable with respect to the piston rod after detachment of the bearing by destroying the at least one predefined breakage point during or after assembly. Thus, only one single component has to be handled during assembly which in use fulfils the function of two separate components.

According to a preferred embodiment, the driver is a tubular element having a distal portion engaging a nut interposed between the housing and the driver, and a proximal portion which at least partly surrounds a tubular portion of the button. Preferably, one of the housing and the driver comprises at least one spline and the other of the housing and the driver comprises a threaded portion with the nut interposed between the housing and the driver, wherein the nut comprises at least one protrusion engaging the at least one spline and a thread engaging the threaded portion, and wherein the threaded portion of the housing or the driver comprises a rotational end stop. If the nut abuts the rotational end stop, further movement of the nut in the thread is prevented which thus prevents further rotation of the driver relative to the housing which is required during dose setting. Thus, the nut may be used to limit the settable dose. This is e.g. required to prevent setting a dose exceeding the amount of medicament in the cartridge.

Preferably, the housing comprises an outer body and an inner body with the cartridge holder being releasably coupled to the inner body. The inner body may be rotationally and axially constrained within the outer body such that a cylindrical gap exists between the inner body and the outer body. Preferably, the inner body comprises an outer thread engaging an inner thread of the display member and comprises at least one inner spline engaging a protrusion of a clicker and/or a dose limiter nut.

In a standard embodiment, the splines of the inner body are axially aligned with the pen device. In an alternative embodiment, it is possible to reduce dispense force, increase the velocity ratio and to increase the thread pitch of the display member (i.e. increase of friction coefficient asymptote), by providing the inner body with at least one inner spline which is helically twisted. In other words, the splines are not axially aligned, which results in the driver and the button traveling helically during dose dispensing. This may require adding an over-cap for the button as an additional component preventing relative rotation with respect to a user's hand, typically the thumb, during dose dispensing.

If the driver comprises a first component which is in threaded engagement with a nut and a second component, the first and the second components may be operatively coupled together in a releasable manner. It is preferred that when a user sets a dose by rotating the button, both the first component and the second component of the driver rotate together. Further, when a user resets the device, the first component of the driver is preferably decoupled from the second component of the driver and the first component is allowed to rotate with respect to the housing and with respect to the second component. The nut may be part of a dose limiter for preventing the setting of a dose, which exceeds the amount of liquid left in a cartridge of the drug delivery device. Thus, a simple and yet reliable resetting mechanism is provided by splitting the driver into two components.

The precision of a last dose protection mechanism, i.e. a dose limiter for preventing the setting of a dose, which exceeds the amount of liquid left in a cartridge of the drug delivery device, may be increased by the driver being in threaded engagement with a nut, and the threaded engagement comprises a helical groove having a first pitch provided along a first portion of the driver, a second pitch provided along a second portion of the driver wherein the first pitch is smaller than the second pitch, and, optionally, a third pitch provided along a third portion of the driver wherein the third pitch is smaller than the second pitch. Preferably, the second and third portions are located close to a rotational hard stop limiting further movement of the nut for preventing the setting of a dose, which exceeds the amount of liquid left in a cartridge of the drug delivery device. The pitch of the first portion may be selected small to reduce the axial length of the device. The increased pitch of the second portion results in a higher axial displacement of the nut relative to the driver such that the nut may pass a relatively large and thus robust rotational hard stop.

The drug delivery device may further comprise a clicker producing a tactile and/or audible feedback during dose setting, i.e. increasing or reducing the dose. This additional clicker may include a first toothed element rotationally constrained to the housing, a second toothed element rotationally constrained to the driver and a spring biasing the first toothed element and the second toothed element into engagement.

A transparent window may be provided within the housing for allowing a user to view the numbers or the like on the display member indicating the set dose. Preferably, the housing comprises an inner body and an outer body with the window being attached to the housing by first retaining means of the inner body and second retaining means of the outer body.

The basic function of the drug delivery device according to the present invention may include that a dose is selected by rotating a button component, which travels helically during dose setting. A dose may be delivered by pressing on the same button component, which now moves axially during dispensing. Preferably, any dose size can be selected, in predefined increments, between zero and a predefined maximum dose, e.g. 80 units. It is a further advantage if the mechanism permits cancelling of a dose without medicament being dispensed, e.g. by rotation of the button component in the opposite direction to when selecting a dose.

It is preferred if during dose setting the button is rotated which entrains the driver and the display member such that the button, the driver and the display member are moved on a helical path with respect to the housing and the piston rod. Further, during dose dispensing the button is axially displaced which entrains the driver and the display member such that the button, the driver and the display member are axially moved with respect to the housing and the piston rod, with the display member and the piston rod rotating with respect to the housing, the button and the driver.

To prevent malfunction or misuse of the device, the dose setting mechanism may be provided with stops preventing dialing of a dose below zero units or dialing of a dose above a maximum dose. Preferably, rotational hard stops are provided, e.g. between the display member and the housing as a zero unit stop and/or as a maximum units stop. If the housing comprises an inner body and an outer body, a first rotational stop may be provided between the inner body and the display member and a second rotational stop may be provided between the outer body and the display member for limiting the rotational movement of the display member relative to the housing. The minimum dose, usually zero units, may be defined by the first rotational stop and the maximum dose, e.g. 60, 80 or 120 units, may be defined by the second rotational stop.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 3 sheets create a "sandwich" shape, held together by interactions between conserved cysteines and other charged amino acids.

There are five types of mammalian Ig heavy chain denoted by α, β, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

A non-limiting, exemplary embodiment of the invention will now be described with reference to the accompanying drawings, in which:

FIG. 1 shows a drug delivery device with a cap attached in accordance with the present invention;

FIG. 2 shows the drug delivery device of FIG. 1 with the cap removed and a dose of 79 units dialed;

FIG. 5a shows the inner body of the drug delivery device of FIG. 1;

FIG. 5b shows a detail of the inner body of FIG. 5a;

FIG. 6 shows the cartridge holder of the drug delivery device of FIG. 1;

FIG. 7a shows a first display member component of the drug delivery device of FIG. 1;

FIG. 7b shows a detail of the first display member of FIG. 7a;

FIG. 8 shows a second display member component of the drug delivery device of FIG. 1;

FIG. 9 shows a first driver component of the drug delivery device of FIG. 1;

FIG. 10 shows a second driver component of the drug delivery device of FIG. 1;

FIG. 11 shows a third driver component of the drug delivery device of FIG. 1;

FIG. 12 shows the last dose nut of the drug delivery device of FIG. 1;

FIG. 13 shows a clutch component of the drug delivery device of FIG. 1;

FIG. 14 shows a first clicker component of the drug delivery device of FIG. 1;

FIG. 15 shows a second clicker component of the drug delivery device of FIG. 1;

FIG. 16 shows the button of the drug delivery device of FIG. 1;

DETAILED DESCRIPTION

Figure 3:
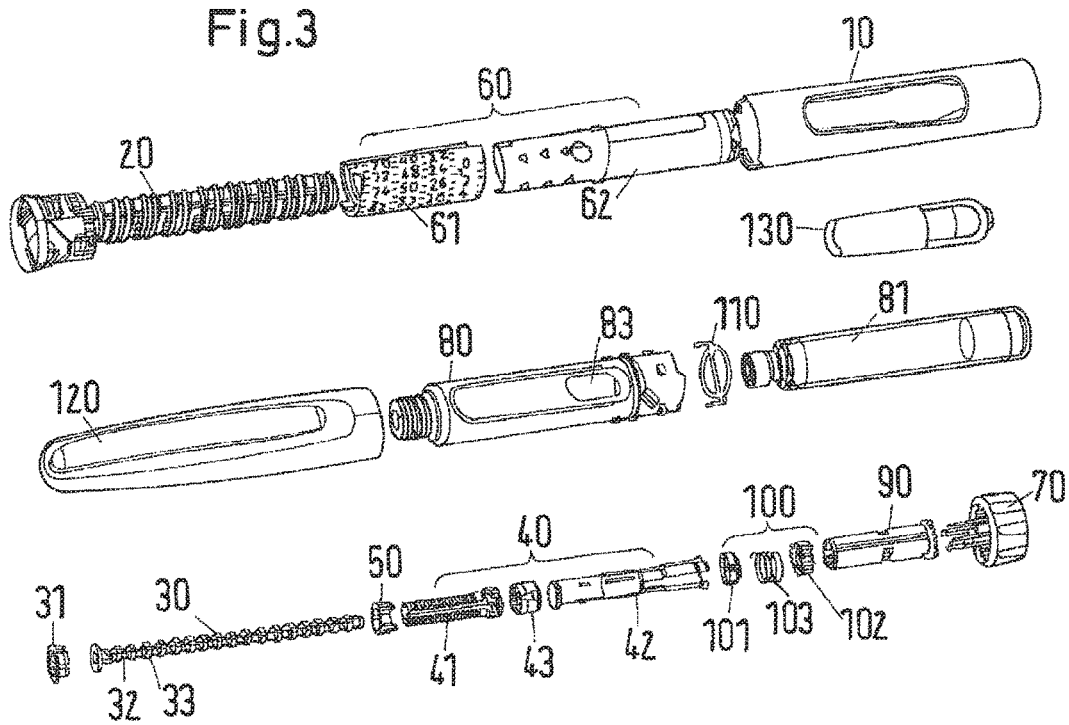
FIG. 3 shows in an exploded view the components of the drug delivery device of FIG. 1.

FIGS. 1 and 2 show a drug delivery device 1 in the form of an injection pen. The device has a distal end (lower end in FIG. 1) and a proximal end (upper end in FIG. 1). The component parts of the drug delivery device 1 are shown in FIG. 3 in more detail. The drug delivery device 1 comprises an outer housing part 10, an inner body 20, a piston rod 30, a driver 40, a nut 50, a display member 60, a button 70, a cartridge holder 80 for receiving a cartridge 81, a clutch 90, a clicker 100, a spring 110, a cap 120 and a window insert 130. A needle arrangement (not shown) comprising a needle hub and a needle cover may be provided as additional components, which can be exchanged as explained above. The piston rod 30 comprises a bearing 31. The driver comprises a distal driver part 41, a proximal driver part 42 and a coupler 43. The display member 60 comprises a number sleeve 61 and a dial sleeve 62. The clicker comprises a distal clicker part 101, a proximal clicker part 102 and a spring 103.

Figure 4:
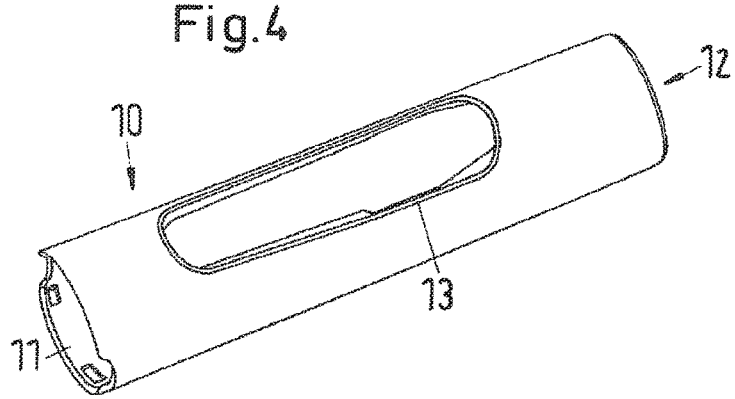
FIG. 4 shows the outer body of the drug delivery device of FIG. 1.

The outer housing part 10, which is shown in FIG. 4, is a generally tubular element having a distal part 11 for attaching the inner body 20 and a proximal part, which is provided with a rotational hard stop 12 on its inner surface (not shown) which contact mating faces of the display member 60 when the maximum units (in this example 80U) stop is engaged. The end face also serves as the end of dose dispense stop for the button 70, and the bore in the end face centers the display member 60 during both dialing and dispense. An aperture 13 is provided for receiving window insert 130. The outer body 10 provides the user with a surface to grip and react against during dispense.

Figure 17:
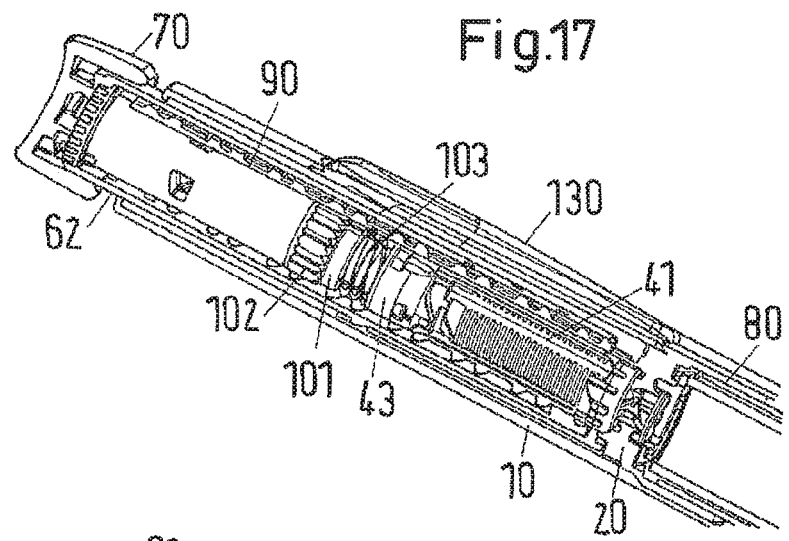
FIG. 17 shows a cut-away view of the proximal part of the drug delivery device of FIG. 1 in a zero unit position with the button released.
Figure 18:
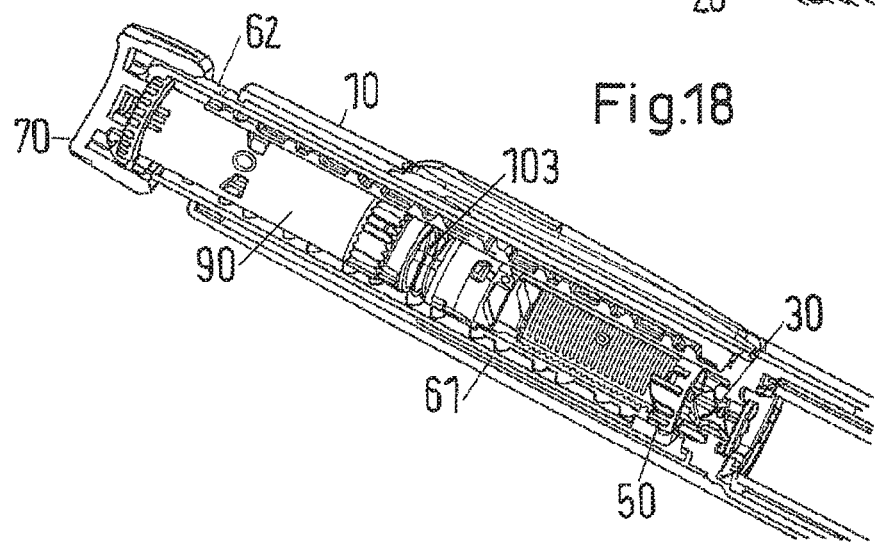
FIG. 18 shows a cut-away view of the proximal part of the drug delivery device of FIG. 1 in a position with some units dialed.
Figure 19:
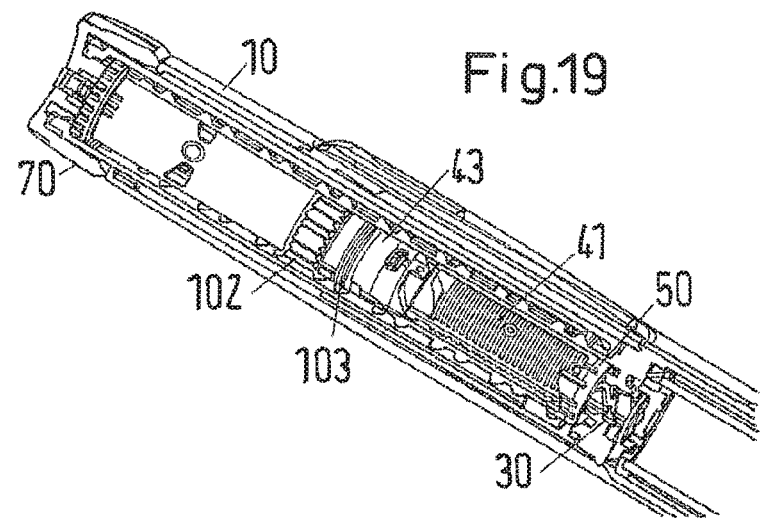
FIG. 19 shows a cut-away view of the proximal part of the drug delivery device of FIG. 1 in a zero unit position with the button pressed.

The inner body 20 is a generally tubular element having different diameter regions. As can be seen in FIGS. 17 to 19, the inner body 20 is received in the outer body 10 and permanently fixed therein to prevent any relative movement of the inner body 20 with respect to the outer body 10. The inner body has the functions to house the drive mechanism within, guiding the clickers and the last dose nut 50 via internal splines, to provide an internal thread through which the piston rod 30 (lead screw) is driven, to support and guide the number sleeve 61 and the dial sleeve 62 on an external thread form, to secure the cartridge holder 80 and to secure the outer body 10 and the window insert 130.

The outermost diameter of the inner body 20 also forms part of the visual design and remains visible when the cap 120 is secured to the cartridge holder 80 as a ring separating the cap 120 from the outer body 10. This visible ring also has depressions which align with the cap snap features on the cartridge holder 80 to indicate that the cartridge holder has been correctly fitted.

An external thread 21 is provided on the outer surface of the inner body 20. Further, splines 22 (FIG. 5b) are provided on the inner surface of the inner body 20. These internal splines 22 guide the proximal part of the clicker 102 axially during both dialing and dispense and also prevent the last dose nut 50 from rotating. Some of the splines may be wider to ensure correct rotational assembly of the internal components, and these wider splines may have a stepped entry to encourage the last dose nut 50 which has mating chamfered external ribs to rotate up against the stop face on the distal drive sleeve 41 during assembly. At the open end shown in FIG. 5b there are additional short splines which together with the alternating long splines 22 are used to rotationally lock the button 70 (dose dial grip) at the end of dispense and serve to increase the strength of the 0U dial stop when the button 70 is depressed. This is achieved by engagement with male spline features 94 on the clutch component 90.

Bayonet features 23 guide the cartridge holder 80 into the mechanism during cartridge replacement, compressing the cartridge bias spring 110, and then back off the cartridge holder 80 a small distance in order to reduce axial play in the mechanism. Snap features inside the inner body 20 lock the cartridge holder 80 rotationally when it has been correctly fitted. The profile of these snaps aims to prevent the user from partially fitting the cartridge holder 80, the cartridge bias spring 110 ejecting the cartridge holder 80 if the snaps have not at least started to engage. A window retention nose 24 retains the window insert 130 when the outer body 10 and window insert 130 assembly is axially inserted onto the inner body 20. Two diametrically opposite stop faces 25 define the rotational end position for the number sleeve 61. This end position is the end of dose detent position for the minimum dose (0U).

The piston rod 30 is an elongate element having two external threads 32, 33 with opposite hand which overlap each other. One of these threads 32 engages the inner thread of the inner body 20. A disk-like bearing 31 is provided at the distal end of the piston rod 30. The bearing 31 may be a separate component as shown in FIG. 3 or may be attached to the piston rod 30 as a one-piece component via a predetermined breaking point.

The piston rod 30 transfers the dispense load from the driver 40 to the bearing 31, creating a mechanical advantage greater than 1:1 by converting the torque generated on the piston rod 30 by the driver 40 thread interface into additional axial load as the piston rod passes through the thread in the inner body 20. The piston rod 30 is reset by pressing on the bearing 31 and this in turn rotates the piston rod back into the inner body 20. This disengages and then rotates the distal drive sleeve 41, resetting the last dose nut 50 back to its starting position on the distal drive sleeve 41.

The driver 40 is a generally tubular element having in the embodiment shown in the Figures three components which are depicted in FIGS. 9 to 11 in more detail.

The distal drive sleeve 41 engages with the piston rod thread 33 to drive the piston rod 30 through the inner body 20 during dose delivery. The distal drive sleeve 41 is also permanently connected to the coupler 43 which in turn is releasably engaged through reset clutch features to the proximal drive sleeve 42. The two halves of the drive sleeve are rotationally and axially connected during dialing and dispense, but are de-coupled rotationally during device reset so that they can rotate relative to each other.

The external thread 44 engages with the last dose nut 50. The thread form has three stages, a shallow first stage (left hand side in FIG. 9) over which the nut 50 travels to count the majority of the units dialed, a fast stage over which the last dose nut moves rapidly axially prior to engaging the stop faces, and a final shallow section which ensures that when the stop faces have engaged, the axial restraint on the nut 50 extends over a reasonable length of thread form. Four equi-spaced stop faces 45 engage with mating stop faces 51 on the last dose nut 50 to limit the number of units that can be dialed. Splines 46 are provided at the proximal end of distal drive sleeve 41 to transfer torque from or to the coupler 43, which may be snapped on the distal drive sleeve 41.

The proximal drive sleeve 42 shown in FIG. 10 supports the clicker components 100 and the clutch 90 and transfers rotational movement from the dose button 90 to the coupler 42 and distal drive sleeve 41.

Teeth features 47 located at the distal end of proximal drive sleeve 42 engage with the reset clutch features on the coupler 43 to connect both halves of the drive sleeve during dialing and dispense. During reset these teeth 47 disengage.

Several splines are provided on the outer surface of proximal drive sleeve 42 engaging with distal clicker part 101, preventing relative rotation during dialing and dispense. Further splines, which are located in the middle region of proximal drive sleeve 42, engage with the clutch 90 component. They may be arranged to be non-rotationally symmetric so that the various clicker components cannot be assembled accidentally upside down.

The proximal portion of proximal drive sleeve 42 has four arms or fingers 48. A hook-like bearing surface 49 exists on the underside (as seen in FIG. 10) of flange segments on the end of the flexible fingers 48. The flexible fingers 48 are separated with gaps or slots that make space for the button 70 to snap to the clutch 90 and also enable these fingers to flex inwards during assembly of the proximal drive sleeve 42 to the dial sleeve 62. After assembly the hooks 49 retain the proximal drive sleeve 42 relative to the dial sleeve 62 under the reaction force from the spring 103. During dispense the button 70 depresses the spring 103 via the clutch 90 and the clicker components and this spring 103 is reacted through the coupler 43 to the proximal drive sleeve 42 which then through these bearing surfaces applies axial load to the dial sleeve 62. This axial load drives the dial sleeve 62 and hence number sleeve 61 along the helical thread of the inner body 20, back into the body of the device, until the 0U stop faces on the number sleeve 61 contact the inner body 20.

The coupler 43 shown in FIG. 11 rotationally couples the two halves of the drive sleeve together during dialing and dispense, whilst allowing them to de-couple during reset. The coupler 43 has to also transfer the last dose protection stop load from the proximal drive sleeve 42 to the distal drive sleeve 41. Two sets of teeth are provided in the coupler 43 for engaging teeth 46 and teeth 47, respectively. The coupler 43 is snapped onto distal drive sleeve 41 allowing limited relative axial movement with respect to the proximal drive sleeve 42.

The nut 50 is provided between the inner body 20 and the distal drive sleeve 41 of driver 40. Stop faces 51 are located on the proximal face of last dose nut 50 to limit the number of units that can be dialed if the stop faces 51 contact stops 45 of distal drive sleeve 41. The function of the last dose nut 50 is to prevent the user from dialing beyond a finite amount. This limit is based on the dispensable volume of the cartridge 81 and when reached, the user must replace the cartridge 81 and reset the device.

External ribs 52 of the nut 50 engage splines 22 of inner body 20. An internal thread 53 of the nut engages the external thread 44 of distal drive sleeve 41. As an alternative, splines and ribs could be provided on the interface between the nut 50 and the driver 40 and threads could be provided on the interface between the nut 50 and the inner body 20. As a further alternative, the nut 50 may be designed as e.g. a half nut.

The display member 60 is a generally tubular element which is composed of number sleeve 61 and dial sleeve 62 which are snapped together during assembly to axially and rotationally constrain these two components, which thus act as a single part.

The main functions of the number sleeve 61 depicted in FIG. 8 are to provide a surface onto which dose numbers can be printed to display the dialed dose, to guide the helical path of the internal mechanism during dialing to follow the helical thread form on the piston rod 30 when threaded to the inner body 20 and to attach to the dial sleeve 62. The number sleeve 61 is designed to be fully enclosed in the outer body 10 during dialing and dispense and therefore only the dialed dose is visible to the user through the window aperture. The number sleeve has a 0U (minimum dose) stop face 63 to limit its travel when dialed in but the 80U (maximum dose) stop faces that limit the dialed out condition are located on the dial sleeve 62. At the end of each dispense stroke, this stop face 63 engages with mating surface 25 on the inner body 20 to limit the rotational position of the number sleeve 61.

A helical drive face 64 forms a thread that guides the number sleeve 61 during dialing and dispense to follow the helical path 21 on the inner body.

The dial sleeve 62 is assembled to the number sleeve 61 such that once assembled, no relative movement is allowed. The parts are made as separate components to enable both molding and assembly. Also, whereas the number sleeve 61 is preferably white to give contrast for the e.g. black dose numbers, the dial sleeve 62 color can be chosen to suit the aesthetics or perhaps to distinguish the drug type.

At the proximal end, the dial sleeve 62 has internal clutch features 65 that engage with the clutch component 90 during dialing and disengage from the clutch during dispense. These clutch features 65 rotationally lock the dial sleeve 62 to the clutch 90 during dialing and when the 0U and 80U stops are engaged. When the button 70 is depressed these clutch features disengage to allow the clutch 90 and drive mechanism to move axially whilst the dial sleeve 62 and number sleeve 61 spin back to the 0U start position.

The dial sleeve 62 rotates out during dialing through its engagement with the clutch 90 and number sleeve 61, and rotates back in during dispense under the axial force applied by the proximal drive sleeve 42 to a flange-like bearing face 66 on the end of the dial sleeve. This bearing face 66 engages with the flexible arms 48 of the proximal drive sleeve 42 during dispense. Two diametrically opposite faces 67 engage with the outer body 10 when the maximum dose (e.g. 80U) has been dialed, forming the maximum dose stop faces.

A ratchet arm 68 engages with ratchet features on the button 70 (dose dial grip) to provide audible feedback during dispense, giving one click per unit delivered. Further, this prevents the user from gripping and rotating the number sleeve 61 outwards from a partially dialed out position whilst holding the button 70 pressed in. This would back wind the piston rod 30 which would result in an under dose on the subsequent dialed dose. It may further strengthen the 0U stop.

The button 70 which is shown in FIG. 16 serves as a dose dial grip and is retained by the clutch 90 to transfer the actions of the user to the clutch. It also carries ratchet teeth 71 that engage the ratchet arm 68 on the dial sleeve 62, which serves as the dispensing clicker giving audible feedback (ratchet clicks), and an end face 72 which serves as the dose completion stop face with the outer body 10. This end face 72 thus serves to define the end position during dispense when it contacts the outer body 10 to provide a very positive stop improving dose accuracy.

A central sleeve-like portion of button 70 is provided with four arms 73 having hook-like snap features 74 at their respective distal ends. The arms 73 form splined surfaces engaging with the clutch 90 to transfer torque from the button 70 through the clutch to the dial sleeve 62 and proximal drive sleeve 42. The snap features 74 engage apertures in the clutch 90 and are designed with angled undercut faces to maintain engagement when an axial load is applied to pull the button 70 out of the pen body 10. The space between arms 73 defines pockets giving clearance for the flexible arms 48 of proximal drive sleeve 42 to slide freely relative to the button 70 and clutch 90 when the button 70 is depressed and released during dose dispense.

The cartridge holder 80 attaches to the inner body 20 with a bayonet connection 82 and houses the glass ampoule or cartridge 81 containing the medication to be dispensed. The cartridge holder 80 includes an aperture 83 in the rear face (as seen in FIG. 6) which if gripped by the user prevents the ampoule from falling out when the cartridge holder is removed from the inner body 20. The front face is printed with a dose number scale. The threaded distal end 84 is used to attach disposable pen needles.

A tubular clutch 90 is provided between the display member 60 and the button 70. The clutch is fixed relative to and retains the button 70 and together they travel axially relative to the proximal drive sleeve 42 when the button 70 is depressed during dispense, disengaging the clutch teeth from the dial sleeve 62. It also transfers torque from the button to the proximal drive sleeve 42, and the dialing and 0U/80U stop loads from the button via the clutch teeth to the dial sleeve and number sleeve.

Drive sleeve splines 91 provided on an inner surface of the clutch engage with the proximal drive sleeve 42. At the distal end face, clutch biasing teeth 92 are provided which mate with similar teeth 109 on the proximal clicker part 102 to ensure that in the button out position (dialed dose) the clutch is locked in rotation to the proximal clicker part 102 under the biasing action of the clutch spring 103. The teeth 92 are shallow in height to prevent the proximal clicker part 102 from engaging with splines on the proximal drive sleeve 42 during dialing. Four snap apertures 93 serve to retain the snap features 74 of button 70. Near its proximal end, the clutch has splines 94 which at the end of dispense with the button 70 depressed lock to the inner body 20 to prevent the user from rotating the button 70 below the 0U position.

Clutch teeth 95 engage with clutch teeth 65 of the dial sleeve to rotationally couple the button 70 via the clutch to the number sleeve 61. During dispense the clutch is moved axially so as to disengage these clutch teeth 95 releasing the dial sleeve 62 to rotate back into the device whilst the clutch 90 and hence driver 40 move axially to dispense the dose.

The clicker 100 comprises a distal clicker part 101, a proximal clicker part 102 and a spring 103. The clutch spring 103 serves to bias the button 70 out so that at the end of a dose the button 70 pops out, re-engaging the clutch 90 with the dial sleeve 62 ready for dialing. Further, it provides the spring force for the clicker components to act as clickers and also as detent positions for the number sleeve 61. In addition, it holds the two halves of the drive sleeves 41, 42 in rotational engagement during dialing and dispense, whilst allowing them to disengage during device reset.

The distal clicker part 101 is permanently splined to the proximal drive sleeve 42 and engages with the proximal clicker part 102 which in turn is splined to the inner body 20. During dialing when the drive sleeve is rotated relative to the inner body, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the dispense load and therefore prevent relative rotation between the proximal drive sleeve 42 and inner body 20, driving the piston rod forwards to deliver the dose. The splines 104 on the inner bore rotationally couple the distal clicker part 101 to the proximal drive sleeve 42 at all times, but allow free axial movement when the button 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body during both dialing and dispense, providing clicks during dialing and locking the proximal drive sleeve 42 in rotation during dispense. Additional cylindrically shaped splines 108 also couple the proximal clicker part 102 rotationally to the proximal drive sleeve 42 when the button 70 is depressed, this preventing the user from dialing past 80 units with the button depressed. Proximal clicker part 102, in addition to the primary clicker teeth 106, has clutch biasing teeth 109 on the opposite end face. These teeth mate with similar teeth 92 on the clutch to ensure that in the button out position (dialed dose) the clutch is locked in rotation to the proximal clicker part 102 under the biasing action of clutch spring 103.

The cartridge bias spring 110 is assembled as two components one after the other, the lower first and the upper second. The spring combination serves to apply an end load to the cartridge 81 at extremes of tolerance so as to bias it forwards onto the end face of the ferrule in the cartridge holder 80. This ensures that when the user removes and attaches a needle, the friction between the needle cannula and septum of the cartridge does not move the cartridge 81 axially relative to the cartridge holder 80. The bias spring 110 also acts to provide a force against which the user has to connect the cartridge holder 80 and this may add to the tactile feedback of this bayonet joint. The spring 100 also serves to eject the cartridge holder 80 if the cartridge holder is not rotated into a secure position, highlighting this error to the user.

The cap 120 serves to protect the cartridge holder 80 from damage and the cartridge 81 itself from dust dirt ingress on to the area around the septum. The cap is designed to accommodate a standard pen injector needle.

The window insert 130 may include a lens to magnify the dose numbers e.g. by approximately 25% from their printed size. The window insert 130 may be back printed to protect the printed surface from abrasion and also to maximize the light entering through the window aperture, giving uniform illumination of the dose numbers and white area around these numbers. Arrows may be printed adjacent to the window aperture that indicate the dose dialed.

In the following, the function of the drug delivery device and its components will be explained in more detail with reference to FIGS. 17 to 19.

To use the device, a user has to select a dose. In the start (at rest) condition as shown in FIG. 17 the display member 60 indicates the number of doses dialed to the user. The number of dialed units can be viewed through the dose window 130 in the outer body 10. Due to the threaded engagement between the display member 60 and the inner body 20 rotation of the button 70 in a clockwise fashion causes the display member 60 to wind out of the device and incrementally count the number of units to be delivered. FIG. 18 shows an intermediate stage of dialing (e.g. 7 of 80 units).

During dose setting button 70, driver 40 and display member 60 are rotationally locked together via clutch 90. Further, button 70, driver 40 and display member 60 are axially coupled. Thus, these three components wind out of the outer housing 10 during dose setting. Clockwise rotation of the button 70 causes the driver 40 to rotate and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

The last dose nut 50 provides the function of counting the number of dispensed units. The nut 50 locks the device at the end of cartridge life and as such no more drug can be dialed by the user. The last dose nut 50 and the driver 40 are connected via a threaded interface as explained above. Further, the last dose nut 50 is assembled into splines 22 such that the nut 50 and the inner body 20 are rotationally locked together (at all times). Rotation of the driver 40 during dialing causes the nut 50 to advance along the thread 44. The nut 50 is free to slide axially within the inner body 20 at all times which allows advancement of the nut. The change in pitch of thread 44 shown in FIG. 9 towards the final doses axially accelerates the advancement of the nut 50 towards the end of cartridge life lockout condition. At the end of life condition, the stop features 51 of the last dose nut 50 contact the corresponding features 45 on the driver 40. The splined contact with inner body 20 reacts any torque transmitted by these stop features 45.

With the desired dose dialed, the device 1 is ready for dose dispensing. This basically requires pushing button 70 which will result in a disengagement of the clutch 90 from dial sleeve 62 thus allowing relative rotation between the display member 60 and the button 70. In all conditions the driver 40 and the button 70 are rotationally locked together by engagement of arms 73 and fingers 48 and by splines 91 engaging corresponding splines on proximal drive sleeve 42. Thus, with the clutch 90 disengaged (button 70 pushed in) button 70 and driver 40 are rotationally locked together with the button 70, the driver 40 and the display member 60 still being axially coupled.

When dispensing a dose, the dose button 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the mechanism is forced to move axially whilst the dial sleeve 62 and number sleeve 61 are free to spin back into the outer housing 10. The interaction of mating threads between the piston rod 30, driver 40 and inner body 20 delivers a mechanical advantage of 2:1. In other words, axially advancing driver 40 causes the piston rod 30 to rotate which due to the threaded engagement of piston rod 30 with the inner body 20 advances the piston rod. During dose dispensing dispense clicker 68, 71 is active which involves button 70 and display member 60. The dispense clicker provides primarily audible feedback to the user that drug is being dispensed.

The end of this step is shown in FIG. 19. At this point the dose is complete and when the user removes the force from the end of the dose button 70, the clutch spring 103 pushes this dose button 70 rearwards, re-engaging the teeth 65 and 95 between the clutch and the dial sleeve.

Resetting the device starts with removal of the cartridge holder 80 and replacing an empty cartridge with a full cartridge 81. As the cartridge holder is re-attached, the bung of the new cartridge contacts bearings 31, thus pushing piston rod 30 back into the housing. Initially, the piston rod 30 screws into the inner body 20, thereby axially disengaging the coupler 43 from the proximal drive sleeve 42 against the biasing force of spring 103. Once disengaged the coupler 43 is free to start rotating together with distal drive sleeve 41 and continues to do so as the cartridge holder 80 is moved axially into engagement with the inner body 20. Thus, the distal drive sleeve 41 rotates with respect to the proximal drive sleeve 42 which is still rotationally constrained in inner body 20 as clicker parts 101 and 102 are pressed together by compressed spring 103. As the distal drive sleeve 41 rotates, last dose nut 50 is reset to its (distal) start position. Coupling the cartridge holder 80 to inner body 20 backs off the mechanism due to the bayonet structure 23 allowing re-engagement of the proximal drive sleeve 42 with coupler 43 and thus the distal drive sleeve 41.

The invention claimed is:

1. A reusable drug delivery device for selecting and dispensing a number of user variable doses of a medicament, comprising;
   a housing;
   a cartridge holder removably coupled to the housing;
   a piston rod contained within the housing and movable in a distal direction relative to the cartridge holder during dose dispensing;
   a driver coupled to the piston rod and comprising a distal drive sleeve and a proximal drive sleeve which are rotationally coupled during dose setting and during dose dispensing and which are rotationally decoupled during resetting of the device;
   a display member; and
   a button rotationally coupled to the driver, wherein during dose setting the driver, the button and the display member are rotated relative to the housing and move on a helical path proximally away from and with respect to the housing and the piston rod, and during dose dispensing the driver, the button, and the display member are axially moved relative to the housing and the piston rod while the display member and the piston rod rotate with respect to the button, the housing, and the driver,
   wherein the piston rod moves in a proximal direction during resetting when the distal drive sleeve and the proximal drive sleeve are decoupled.

2. The drug delivery device of claim 1 where the proximal drive sleeve and distal drive sleeve are axially connected during dose setting and during dose dispensing.

3. The drug delivery device of claim 1 where the proximal drive sleeve and distal drive sleeve are decoupled during resetting such that the distal drive sleeve can rotate relative to the proximal drive sleeve, which is rotationally fixed relative to the housing.

4. The drug delivery device of claim 1 further comprising a clutch spring that biases the distal drive sleeve and proximal drive sleeve together during dose setting and during dose dispensing.

5. The reusable drug delivery device of claim 1 where during resetting the decoupling of the distal drive sleeve and the proximal drive sleeve permits the piston rod to be pushed back into the housing such that an empty cartridge can be removed from the cartridge holder and replaced with a full cartridge.

6. The drug delivery device of claim 1 further comprising a last dose nut rotatably coupled to the distal drive sleeve and having a distal start position.

7. The drug delivery device of claim 6 where rotation of the distal drive sleeve during resetting rotates the last dose nut to the distal start position.

8. The drug delivery device of claim 1 where the piston rod has a start position and rotates and moves axially from the start position in a first direction during dose dispensing and during resetting rotates moves axially to the start position in a second direction opposite the first direction.

9. The drug delivery device of claim 8 where movement of the piston rod in the second direction overcomes the biasing of a clutch spring and decouples a coupler from the proximal drive sleeve allowing the distal drive sleeve to rotate relative to the proximal drive sleeve.

10. The drug delivery device of claim 1 further comprising a coupler.

11. The drug delivery device of claim 10 where the proximal drive sleeve has a distal end comprising teeth that engage the coupler during dose setting and during dose dispensing, and disengage the coupler during resetting.

12. The drug delivery device of claim 10 where the coupler is permanently coupled to the distal drive sleeve and relaeasbly engaged with the proximal drive sleeve.

13. A method of resetting a reusable drug delivery device, where the drug delivery device comprises;
   a housing;
   a cartridge holder removably coupled to the housing;
   a piston rod contained within the housing and movable in a distal direction relative to the cartridge holder during dose dispensing;
   a driver coupled to the piston rod and comprising a distal drive sleeve and a proximal drive sleeve which are rotationally coupled during dose setting and during dose dispensing and which are rotationally decoupled during resetting of the device;
   a clutch spring biasing the distal drive sleeve and the proximal drive sleeve into a rotationally coupled engagement during dose setting and during dose dispensing,
   a display member; and
   a button rotationally coupled to the driver, wherein during dose setting the driver, the button and the display member are rotated relative to the housing and move on a helical path proximally away from and with respect to the housing and the piston rod, and during dose dispensing the driver, the button, and the display member are axially moved relative to the housing and the piston rod while the display member and the piston rod rotate with respect to the button, the housing, and the driver,
where the method comprises:
decoupling the cartridge holder from the housing to remove the clutch spring biasing and allow decoupling of the distal drive sleeve from the proximal drive sleeve;
inserting a cartridge of medicament having a bung into the cartridge holder;
engaging the bung with the piston rod to push and rotate the piston rod in a proximal direction causing rotation of the distal drive sleeve relative to the proximal drive sleeve; and
coupling the cartridge holder with the housing such that the clutch spring biases the distal drive sleeve and the proximal drive sleeve into the rotationally coupled engagement.

* * * * *

UNITED STATES PATENT AND TRADEMARK OFFICE
CERTIFICATE OF CORRECTION

PATENT NO. : 10,265,479 B2  
APPLICATION NO. : 15/138533  
DATED : April 23, 2019  
INVENTOR(S) : David Aubrey Plumptre and Thomas Frederick Osman It is certified that error appears in the above-identified patent and that said Letters Patent is hereby corrected as shown below:

In the Claims

Column 19, Line 25, Claim 12, delete "relaeasbly" and insert -- releasably --

Signed and Sealed this  
Thirtieth Day of July, 2019

Andrei Iancu  
*Director of the United States Patent and Trademark Office*